United States Patent [19]
Rubin et al.

[11] Patent Number: 6,146,614
[45] Date of Patent: Nov. 14, 2000

[54] METHOD FOR DETERMINING LYMPHOCYTE DISTRIBUTION AND TRAFFICKING IN MAMMALS USING IMAGING

[75] Inventors: Robert H. Rubin, Brookline; Alan J. Fischman, Boston, both of Mass.; David Baltimore, Pasadena, Calif.

[73] Assignees: Massachusetts Institute of Technology, Cambridge; The General Hospital Corporation, Boston, both of Mass.

[21] Appl. No.: 08/886,578

[22] Filed: Jul. 1, 1997

Related U.S. Application Data

[60] Provisional application No. 60/021,083, Jul. 2, 1996.

[51] Int. Cl.$^7$ .......................... A61K 51/10; A61K 49/04; A61B 5/055
[52] U.S. Cl. ....................... 424/1.49; 424/1.69; 424/9.34; 424/9.4; 436/543; 436/545
[58] Field of Search ................................... 436/543, 545; 424/1.49, 1.69, 9.34, 9.4

[56] References Cited

U.S. PATENT DOCUMENTS

| | | | |
|---|---|---|---|
| 5,277,892 | 1/1994 | Rhodes .................................. | 424/1.69 |
| 5,674,680 | 10/1997 | Saksela et al. .............................. | 435/5 |

OTHER PUBLICATIONS

Grimfors et a., Tumour imaging of indium–111 oxine labelled autologous lymphocytes as a staging method in Hodgkin's disease. Eur. J. Haematol. 276–283, 1989.
Kinne et al., Imaging rheumatoid arthritis joints with technetium–99m labelled anti–CD4–and non–specific monoclonal antibodies. Eur. J. Nucl. Med. 21(2):176–180, 1994.
Loutfi et al., In vivo imaging of rat lymphocytes with an indium 111–labelled anti–T cell monoclonal antibody: a comparison with indium 111–labelled lymphocytes, Eur. J. Nucl. Med. 16:69–76, 1990.
Halpern et al., Scintigraphy with In–111–labeled Monoclonal Antitumor Antibodies:Kinetics, Biodistribution and Tumor Detection Radiology 168:529–536 (1988).
Deland and Goldenberg, Diagnosis and Treatment of Neoplasms with Radionuclide–Labeled Antibodies, Seminars in Nuclear Medicine 15:2–11 (1985).
Signore et al., A radiopharmaceutical for imaging areas of lymphocytic infiltration:$^{123}$I–interleukin–2. Labelling procedure and animal studies Nuclear Med. Communications 13:713–722 (1992).
Knochel et al., Diagnosis of Abdominal Abscesses with Computed Tomography, Ultrasound and $^{111}$In Leukocyte Scans, Radiology 137:425–432 (1980).
Krejcarek and Tucker, Covalent attachment of chelating groups to macromolecules, Biochem Biophys Res Commun 77:581–585 (1977).
Larson et al., Imaging of Melanoma with I–131–Labeled Monoclonal Antibodies, J. Nucl Med. 24:123–129, (1983).
Carroll et al., Ultraconography and Indium 111 White Blood Cell Scanning for the Detection of Intraabdominal Abscesses, Radiology 140:155–160 (1981).

McAfee and Thakur, Survey of Radioactive Agents for In Vitro Labelling of Phagocytic Leukocytes, J. Nucl. Med. 17:480–487 (1976).
Loufti et al., In vivo imaging of rat lymphocytes with an indium 111–labelled anti–T cell monoclonal antibody: a comparison with indium 111–labelled lymphocytes, Eur. J. of Nuclear Med. 16:69–76 (1990).
Rubin et al., $^{111}$In–labeled nonspecific immunoglobulin scanning in the detection of focal infection, N Engl J Med. 321:935–40 (1989).
Oyen et al., Detection of Subacute Infectious Foci with Indium–111–Labeled Autologous Leukocytes and Indium–111–Labeled Human Nonspecific Immunoglobulin G:A Prospective Comparative Study, J. of Nuclear Med. 32:1854–1860 (1991).
Saksela et al., Human immunodeficiency virus type 1 mRNA expression in peripheral blood cells predicts disease progression independently of the numbers of CD4 $^+$lymphocytes, PNAS USA 91:1104–1108 (1994).
Khaw et al., Monoclonal antibody to cardiac myosin:imaging of experimental myocardial infection, Hybridoma 3:11–23 (1984).
Sfakianakis et al., Comparisons of Scintigraphy with In–111 Leukocytes and Ga–67 in the Diagnosis of Occult Sepsis, J. Nucl Med. 23:618–626 (1982).
Ghobrial et al., In Vivo Use of Monoclonal Antibodies against Murine T Cell Antigens, Clin. Immunol. & Immunopathol. 52:486–506 (1989).
Larson et al., Localization of $^{131}$I–Labeled p97–specific Fab Fragments in Human Melanoma as a Basis for Radiotherapy, J. of Clin. Investigation 72:2101–2114 (1983).
Harlow and Lane, Antibodies a Laboratory Manual, Cold Spring Harbor Laboratory, Chapter 8, Storing and Purifying Antibodies, pp.:283–318 (1988).
Thakur, M., Cell Labeling:Achievement, Challenges and Prospects, J of Nuclear Med 22:1011–1014 (1981).
Dialynas et al., Characterization of the murine Tcell surface molecule, designated L3T4, identified by monoclonal antibody GK1.5:Similarity of L3T4 to the human Leu–3/T4molecule, J. Immunol. 131:2445–51 (1983).

*Primary Examiner*—Donna C. Wortman
*Attorney, Agent, or Firm*—Clark & Elbing LLP; Kristina Bieker-Brady

[57] ABSTRACT

Methods for determining lymphocyte distribution and trafficking in a mammal are described. Either a labeled ligand capable of interacting specifically with the lymphocytes of the mammal is administered to the mammal so that the labeled ligand interacts in vivo with the lymphocytes, resulting in labeled lymphocytes, or, the labeled ligand is contacted with the lymphocytes in vitro so that the labeled ligand interacts with the lymphocytes resulting in labeled lymphocytes, and these labeled lymphocytes are administered to the mammal. The distribution or trafficking of the labeled lymphocytes in the mammal is determined by imaging. Methods for diagnosing the degree of progression of a disease in a mammal by determining the mammal's lymphocyte distribution or trafficking pattern, for monitoring the response to a therapy in mammal having a disease, for evaluating the ability of an agent to alter the distribution or trafficking of lymphocytes, and for identifying an agent useful for treating a mammal having a disease, are also described.

60 Claims, No Drawings

METHOD FOR DETERMINING LYMPHOCYTE DISTRIBUTION AND TRAFFICKING IN MAMMALS USING IMAGING

This application claims the benefit of U.S. Provisional Application No. 60/021,083 filed Jul. 2, 1996.

FIELD OF THE INVENTION

The present invention relates to methods for determining lymphocyte distribution and trafficking in mammals using imaging techniques, and using such determinations for diagnosing the progression of various diseases, e.g., HIV infection, autoimmune diseases, infectious diseases and malignancies, for monitoring the response to various therapies for such diseases, and for identifying agents useful for treating individuals infected with such diseases.

BACKGROUND OF THE INVENTION

Infection by the human immunodeficiency virus (HIV) has grown to epidemic proportions, affecting about one to two million persons in the United States, and about eight to ten million persons worldwide. Lymphocytes having the CD4 antigen on their surface appear to be the major target of this virus. HIV-infected CD4-positive lymphocytes have been reported to be located in the peripheral blood, the lymph nodes and other internal lymphoid organs.

Enumeration of CD4-positive cells in the peripheral blood has been the most widely used test for monitoring HIV-induced immune dysfunction, as well as serving as a surrogate marker for evaluating anti-viral drug efficacy. The peripheral blood CD4 cell count, however, has been reported to have only limited usefulness. It is now believed that major functional alterations in immunity may be unrecognized by peripheral blood CD4 cell enumeration alone. For example: (i) there is considerable day to day variability in peripheral blood CD4 counts within a given individual; (ii) peripheral blood CD4 counts do not provide information about lymphocyte function; (iii) the peripheral blood comprises only about 2–5% of the total body lymphoid tissue; and (iv) important changes in CD4 cell trafficking and distribution may not be represented by measurements that sample only the peripheral blood. In addition, serial determination of CD4 levels as a marker for anti-viral drug efficacy has been reported to give disappointing results, i.e., maintenance or elevations in CD4 cell counts achieved in association with antiviral therapy have often not been predictive of prolonged life or decreased incidence of opportunistic infection.

The presence of lymphocytes in the lymphoid organs can be determined in certain situations using the technique of biopsy. Biopsy, however, is only of limited value because it generally cannot be used routinely and generally is restricted to easily-accessible lymph nodes.

Thus, there is a compelling need for a non-invasive test that can assess immune function, and that can provide an index of the totality of lymphocyte distribution and trafficking throughout the body, i.e., in other tissues as well as the peripheral blood.

There also is a need for such a test in evaluating individual patients with autoimmune diseases, particularly those in which immunomodulating therapy might be useful, e.g., rheumatoid arthritis or multiple sclerosis, or in patients with certain infections or malignancies.

SUMMARY OF THE INVENTION

It is an object of the invention to provide a safe, effective and easy method for determining lymphocyte distribution and trafficking in an individual.

It is yet another object of the invention to provide a method for determining lymphocyte distribution and trafficking which does not involve an invasive procedure.

It is yet another object of the invention to utilize imaging techniques to determine an individual's lymphocyte distribution and trafficking patterns.

It is yet another object of the invention to evaluate the progression of an HIV infection in an individual by determining the individual's lymphocyte and trafficking patterns.

It is yet another object of the invention to evaluate the efficacy of putative anti-HIV therapies by assessing the therapies' effect on lymphocyte distribution and trafficking patterns in individuals.

Still another object of the invention is to alleviate the symptoms of HIV infection by administering an agent which alters the lymphocyte distribution or trafficking patterns in the infected individual.

According to the invention a method for determining lymphocyte distribution in a mammal is provided. A mammal having lymphocytes is provided, and a labeled ligand capable of interacting specifically with the lymphocytes is provided. The labeled ligand is administered to the mammal under conditions which allow the labeled ligand to interact with the lymphocytes so as to result in labeled lymphocytes. The distribution of the labeled lymphocytes in the mammal is determined by imaging.

In certain embodiments, the mammal has a disease, e.g., an HIV infection, an autoimmune disease, an infectious disease, or a malignancy.

The lymphocytes can be, e.g., B cells or T cells. For certain embodiments, it is preferred that the lymphocytes are CD4-positive cells or CD8-positive cells. The ligand can be, e.g., an antibody, e.g., a polyclonal antibody or a monoclonal antibody, e.g., anti-CD4 monoclonal antibody, an antibody fragment, a recombinant antibody, a peptide, a peptide mimetic, a carbohydrate or a glycoprotein. The label in the labeled ligand can be, e.g., a gamma emitter, e.g., indium-111, technetium-99m, technetium-99 or iodine-123, a positron emitter, e.g., fluorine-18, carbon-11, or iodine-124, a magnetic material, e.g., gadolinium, superparamagnetic substances, or hydrated iron oxide particles, or a density based contrast material. The imaging can be, e.g., radioimaging, magnetic resonance imaging or computed tomographic imaging. The imaging can consist of single or serial scans, and can be total or partial body scans of the mammal.

Another aspect of the invention is a method for determining lymphocyte trafficking in a mammal. A mammal is provided. A cell population having lymphocytes is provided, and a labeled ligand capable of interacting specifically with the lymphocytes is provided. The lymphocytes are contacted in vitro with the labeled ligand under conditions which allow the ligand to interact with the lymphocytes so as to result in labeled lymphocytes. The labeled lymphocytes are administered into the mammal. The trafficking of the labeled lymphocytes in the mammal is determined by imaging.

Another aspect of the invention is a method for diagnosing the degree of progression of a disease in a mammal. The disease can be, e.g., an HIV infection, an autoimmune disease, e.g., rheumatoid arthritis, multiple sclerosis, inflammatory bowel disease, systemic lupus erythematosis, or psoriasis, an infectious disease, or a malignancy, e.g., myeloma, lymphoma, leukemia or a solid tumor. A mammal having lymphocytes and infected with such a disease is provided. The lymphocytes, e.g., B cells or T cells, can be any lymphocytes which are affected either directly or indirectly by the disease. In certain embodiments, it is preferred that the lymphocytes are CD4-positive cells or CD8-positive cells. The distribution or trafficking patterns of the leukocytes in the mammal is determined by imaging. The distribution or trafficking patterns are compared to a standard so as to diagnose the degree of progression of the disease.

Another aspect of the invention is a method for monitoring the response to a therapy in a mammal having a disease. A mammal having lymphocytes and having a disease are provided. The mammal is treated with a therapy for the disease. The response of the mammal to the treating step is monitored, by determining whether the therapy alters the distribution or trafficking pattern of the lymphocytes by imaging.

Another aspect of the invention is a method for evaluating the ability of an agent to alter the distribution or trafficking of lymphocytes in a mammal. A mammal having lymphocytes is provided. An agent is provided and administered to the mammal. It is then determined whether the agent alters the distribution or trafficking of the lymphocytes in the mammal. The distribution or trafficking is altered if it differs from a standard distribution or trafficking pattern.

Another aspect of the invention is a method for identifying an agent useful for treating a mammal having a disease, e.g., an HIV infection, an autoimmune disease, an infectious disease, or a malignancy. A mammal, infected with such a disease and having lymphocytes, e.g., T cells or B cells, or CD4-positive or CD8-positive cells, is provided. An agent is provided and administered to the mammal. It is determined if the agent alters the distribution or trafficking pattern of the lymphocytes in the mammal. An alteration in the distribution or trafficking pattern which results in a pattern which is more similar to that of a mammal which does not have the disease is correlated with the agent being useful for treating the mammal infected with the disease.

Another aspect of the invention is the agent obtainable by this method.

Another aspect of the invention is a method of utilizing an agent obtainable by this method to alleviate the symptoms of a disease in a mammal. A mammal having a disease is provided. An agent obtainable by the above described method is provided, and a therapeutically effective amount of the agent is administered to the mammal so as to alleviate the symptoms of the disease in the mammal.

Another aspect of the invention is a method for treating a mammal having a disease. A mammal having a disease, e.g., an HIV infection, an autoimmune disease, an infectious disease, or a malignancy, and having lymphocytes, e.g., T cells or B cells, or CD4-positive or CD8-positive cells, is provided. The mammal is tested for an alteration in the distribution or trafficking of the lymphocytes as compared to a standard. If the distribution or trafficking of the lymphocytes is altered in the mammal having the disease, then a therapeutically effective amount of an agent which results in at least partially normalizing the altered distribution or trafficking of the lymphocytes is administered.

The above and other objects, features and advantages of the present invention will be better understood from the following specification.

DETAILED DESCRIPTION

This invention provides a method for determining lymphocyte distribution in a mammal. A mammal having lymphocytes is provided, and a labeled ligand capable of interacting specifically with the lymphocytes is provided. The labeled ligand is administered to the mammal under conditions which allow the labeled ligand to interact with the lymphocytes so as to result in labeled lymphocytes. The distribution of the labeled lymphocytes in the mammal is determined by imaging.

By mammal is meant a human as well as a non-human mammal. In certain embodiments, the mammal is infected with human immunodeficiency virus (HIV). In other embodiments, the mammal has an autoimmune disease, e.g., rheumatoid arthritis, multiple sclerosis, inflammatory bowel disease, systemic lupus erythematosis, or psoriasis. In yet other embodiments, the mammal has an infectious disease or a malignancy, e.g., myeloma, lymphoma, leukemia, or a solid tumor, e.g., melanoma, renal cell carcinoma or lung cancer.

By lymphocyte distribution is meant the location of the lymphocytes in the body. The location of the lymphocytes in the body includes, e.g., the distribution in the tissues, as well as the peripheral blood. The lymphocyte distribution can be determined for the entire body, or for portions of the body.

Lymphocytes include, e.g., B cells and T cells. Lymphocytes have various surface antigens which define different populations of lymphocytes. Examples include CD3, CD4, CD8 and CD25. In certain embodiments, it is preferred that the lymphocytes are CD4-positive cells or CD8-positive cells. For example, lymphocytes which have the CD4 surface antigen (CD4-positive cells) constitute a prime target for HIV.

The ligand of the invention is capable of interacting specifically with the lymphocytes. For example, the ligand can interact with a specific lymphocyte surface antigen, e.g., CD4. The ligand can be any type of molecule which exhibits such a specific interaction. For example, the ligand can be an antibody, a recombinant antibody or an antibody fragment, e.g., Fab, F(ab')$_2$ or Fab'. The use of whole antibodies can lead to HAMA (human antimouse antibody formation) in certain situations. Certain antibody fragments are preferred because they are less immunogenic due to the absence of the Fc fragment, and therefore, do not result in HAMA. Humanized antibodies can be used in those embodiments in which the lymphocyte distribution is being determined in a human. The antibody can be polyclonal or monoclonal. Preferably, the antibody is a monoclonal antibody. For example, OKT3 (Orthclone), a murine anti-human CD3 monoclonal antibody for human use can be obtained from Ortho Pharmaceutical. Other monoclonal antibodies, e.g., anti-CD4 monoclonal antibody, can be made by standard techniques known to those skilled in the art.

Ligand is also meant to include, e.g., a peptide, a peptide mimetic, a carbohydrate or a glycoprotein. By peptide mimetic is meant a non-peptide compound which resembles in shape and/or charge distribution a particular ligand which is a peptide.

The ligand is labeled. The label of the invention can be any label whose presence in the body can be determined by non-invasive procedures. For example, the label can be a gamma emitter, a positron emitter, a magnetic material, a density based contrast material, or mixtures thereof. Examples of gamma emitters include indium-111, technetium-99m, technetium-99 and iodine-123. Preferably, indium-111 is used. Examples of positron emitters include fluorine-18, carbon-11 and iodine-124. Examples of magnetic materials include gadolinium, superparamagnetic substances, and hydrated iron oxide particles.

Any procedure known to those skilled in the art for labeling the ligand can be used.

Administration of the labeled ligand into the mammal can be accomplished by any method which allows the labeled ligand to interact with lymphocytes in the body so as to result in labeled lymphocytes. These methods include, e.g., injection, infusion, deposition, implantation, oral ingestion or topical administration. Preferably, administration is by injection. Injections can be, e.g., intravenous, intradermal, subcutaneous, intramuscular or intraperitoneal. In certain embodiments, multiple administrations of the ligand are given.

The labeled ligand can be in a liquid, e.g., in dissolved form or colloidal form. The liquid can be a solvent, partial solvent or non-solvent. In many cases, water or an organic liquid can be used.

Preferably, the dose of the labeled ligand is about 0.1 $\mu$g/kg body weight to about 10 $\mu$g/kg body weight, and most preferably is about 1.0 $\mu$g/kg body weight to about 4.0 $\mu$g/kg body weight. The amount of radioactivity depends upon the particular isotope and can be determined by one skilled in the art without undue experimentations. For example, it is preferred to use about 1.5 to about 3.0 mCi/dose of indium-111, about 10 to about 30 mCi/dose of technetium-99, about 5 to about 10 mCi/dose of iodine-123, about 5 to about 10 mCi/dose iodine-124, about 10 to about 20 mCi/dose fluorine-18 and about 20 to about 30 mCi/dose carbon-11.

The administered labeled ligand interacts with the lymphocytes so as to result in labeled lymphocytes. Interacts is meant to include, e.g., binds, complexes or conjugates. It is preferred that the interaction be a direct interaction.

The distribution of the labeled lymphocytes in the body is determined by an imaging technique. By imaging is meant the detection of the distribution of the radiolabel in the body by non-invasive means. Examples of imaging include radioimaging, magnetic resonance imaging and computed tomographic imaging. The presence of gamma emitters can be determined, e.g., by a gamma camera or a single photon emission computed tomography (SPECT) camera. The presence of positron emitters can be determined by, e.g., a positron emission tomographic (PET) camera. The presence of magnetic particles can be determined by, e.g., magnetic resonance imaging (MRI). These imaging techniques are known to those skilled in the art.

In preferred embodiments, the imaging is a total body scan of the mammal, though partial body scans are also included in the invention. The timing after administration of the labeled ligand for a scan can be minutes, hours, days, weeks or months. The particular timing depends upon many factors, including, e.g., the type of label, the amount of label, the behavior of the lymphocytes, and the disease condition. The timing can be determined by one of ordinary skill in the art employing such factors and using no more than routine experimentation. The imaging can be accomplished with a single scan or with serial scans.

This invention also provides a method for determining lymphocyte trafficking in a mammal. A first mammal is provided. A cell population having lymphocytes is provided, and a labeled ligand capable of interacting specifically with the lymphocytes is provided. The lymphocytes are contacted in vitro with the labeled ligand under conditions which allow the ligand to interact with the lymphocytes so as to result in labeled lymphocytes. The labeled lymphocytes are administered into the first mammal. The trafficking of the labeled lymphocytes in the first mammal is determined by imaging.

In certain embodiments, the first mammal is infected with HIV. In other embodiments, the mammal has an autoimmune disease, e.g., rheumatoid arthritis, multiple sclerosis, inflammatory bowel disease, systemic lupus erythematosis, or psoriasis. In yet other embodiments, the mammal has an infectious disease or a malignancy, e.g., myeloma, lymphoma, leukemia, or a solid tumor, e.g., melanoma, renal cell carcinoma or lung cancer.

By lymphocyte trafficking is meant the pattern of migration of the lymphocytes in the body, including the tissues, as well as the peripheral blood. Lymphocyte trafficking can be determined for the entire body, or for portions of the body.

The cell population having lymphocytes can be obtained from the first mammal or from a second mammal. Contacting the lymphocytes in vitro with the labeled ligand is accomplished under conditions which allow the ligand to interact with the lymphocytes so as to result in labeled lymphocytes. An advantage of this invention is that the specific lymphocytes do not need to be isolated in order for them to interact with the ligand. In certain embodiments, the lymphocytes that are contacted in vivo with the labeled ligand are in a mixed cell population. For example, whole blood can be contacted with the labeled ligand so as to result in labeled lymphocytes.

Administration of the labeled lymphocytes into the first mammal can be accomplished by a variety of methods, including, e.g., injection, infusion, deposition, implantation, oral ingestion or topical administration. Preferably, administration is by injection. Injections can be, e.g., intravenous, intradermal, subcutaneous, intramuscular or intraperitoneal. Preferably, the dose of the labeled lymphocytes is lymphocytes present in about 50 to about 75 cubic centimeters of the subject's whole blood such that the appropriate amount of radioactivity is administered. The amount of radioactivty depends upon the isotope used and can by determined by one skilled in the art without undue experimentation. For example, it is preferred to use about 1.5 to about 3.0 mCi/dose of indium-111, about 10 to about 30 mCi/dose of technetium-99, about 5 to about 10 mCi/dose of iodine-123, about 5 to about 10 mCi/dose iodine-124, about 10 to about 20 mCi/dose fluorine-18 and about 20 to about 30 mCi/dose carbon-11. In certain embodiments, multiple administration of the labeled lymphocytes can be used. The imaging of the labeled lymphocytes to determine their trafficking in the mammal is accomplished as described above. Preferably, serial scans are obtained.

The invention also includes a method for diagnosing the degree of progression of a disease in a mammal. The disease can be, e.g., an HIV infection, an autoimmune disease, an infectious disease, or a malignancy. Examples of an autoimmune disease are rheumatoid arthritis, multiple sclerosis, inflammatory bowel disease, systemic lupus erythematosis, and psoriasis. Examples of a malignancy are myeloma, lymphoma, leukemia and a solid tumor, e.g., melanoma, renal cell carcinoma and lung cancer. The invention is particularly useful for diseases in which immunomodulating therapy might be useful. A mammal having lymphocytes and infected with such a disease is provided. The lymphocytes can be any lymphocytes which are affected either directly or indirectly by the disease. Lymphocytes include, e.g., T cells and B cells. In certain embodiments, it is preferred that the lymphocytes are CD4-positive cells or CD8-positive cells. The distribution or trafficking patterns of the lymphocytes in the mammal is determined by imaging. Preferably, these patterns are determined by the methods described above. The distribution or trafficking patterns are compared to a standard so as to diagnose the degree of progression of the disease. The standard can be, e.g., a pattern obtained from an earlier determination of the disease-infected mammal, or a pattern obtained from another mammal not infected with the disease.

The invention also includes a method for monitoring the response to a therapy in a mammal having a disease.

Preferably, the disease is an HIV infection, an autoimmune disease, an infectious disease, or a malignancy. A mammal having lymphocytes and having such a disease is provided. The lymphocytes can be any lymphocytes which are affected either directly or indirectly by the disease. Lymphocytes include, e.g., T cells and B cells. In certain embodiments, it is preferred that the lymphocytes are CD4-positive cells or CD8-positive cells. The mammal is treated with a therapy for the disease. The response of the mammal to the treating step is monitored, by determining whether the therapy alters the distribution or trafficking pattern of the lymphocytes by imaging. Preferably, these patterns are determined by the methods described above. Preferably, the distribution or trafficking patterns are compared to a pattern obtained from an earlier determination of the disease-infected mammal, e.g., prior to the therapy treatment, or an earlier time point after the therapy treatment.

The invention also includes a method for evaluating the ability of an agent to alter the distribution or trafficking of lymphocytes in a mammal. Altering is meant to include directly or indirectly altering the lymphocyte distribution or trafficking patterns. For example, an agent can affect some condition or factor which in turn affects the lymphocyte distribution or trafficking patterns. Lymphocytes include, e.g., T cells and B cells. In certain embodiments, it is preferred that the lymphocytes are CD4-positive cells or CD8-positive cells. A mammal having lymphocytes is provided. In certain embodiments, the mammal is infected with a disease, e.g., an HIV infection, an autoimmune disease, an infectious disease, or a malignancy. In certain embodiments, the mammal has a reduced number of lymphocytes as compared to a normal mammal. For example, individuals infected with HIV often have reduced numbers of CD4-positive cells. An agent is provided and administered to the mammal. It is then determined whether the agent alters the distribution or trafficking of the lymphocytes in the mammal. In preferred embodiments, the distribution and trafficking of the lymphocytes is determined by the methods described above. The distribution or trafficking is altered if it differs from a standard distribution or trafficking pattern. The standard used can be, e.g., the pattern obtained from the same mammal when the test agent is not present in the mammal, or the pattern obtained from another mammal.

The agent being tested can be, e.g., a putative therapeutic agent for a disease, e.g., an HIV infection, an autoimmune disease, an infectious disease or a malignancy, or it can be a putative agent which alters other abnormal states which affect lymphocyte distribution or trafficking, or it can be a putative agent which alters the normal distribution or trafficking of lymphocytes. Agents can include, e.g., proteins, peptides, carbohydrates, polysaccharides, glycoproteins, nucleic acids, and mimetics, fragments or recombinant forms of the above, or any other type of compound which can be administered to the mammal. Agents are also meant to include, e.g., ionizing radiation, non-ionizing radiation and ultrasound. Agents include, e.g., inhibitors or activators of a molecule that is either required for, or inhibits, the synthesis, post-translational modification or functioning of some element involved in the distribution or trafficking of lymphocytes. Agents can, e.g., regulate the spatial or temporal control of expression of a gene product. Agents can include, e.g., cytokines, growth factors, hormones, signaling components, kinases, phosphatases, homeobox proteins, transcription factors, translation factors and post-translation factors or enzymes. Agents can, e.g., make modifications, e.g., chemical, charge or shape modifications, in the lymphocytes or some other element. Agents can, e.g., affect the interaction between two or more cellular or extra-cellular components. The agent can, e.g., act directly or indirectly on the lymphocytes so as to alter the distribution or trafficking of the lymphocytes. The agent can be specific or non-specific for affecting lymphocyte distribution or trafficking. The agents of the invention are meant to include reversible and non-reversible agents.

Administration of the agent can be accomplished by any method which allows the agent to reach its target. These methods include, e.g., injection, infusion, deposition, implantation, suppositories, oral ingestion, inhalation, topical administration, or any other method of administration where access to the target by the agent is obtained. Injections can be, e.g., intravenous, intradermal, subcutaneous, intramuscular or intraperitoneal. Implantation includes inserting implantable drug delivery systems, e.g, microspheres, hydrogels, polymeric reservoirs, cholesterol matrices, polymeric systems, e.g., matrix erosion and/or diffusion systems and non-polymeric systems, e.g., compressed, fused or partially fused pellets. Suppositories include glycerin suppositories. Oral ingestion doses can be enterically coated. Inhalation includes administering the agent with an aerosol in an inhalator, either alone or attached to a carrier that can be absorbed.

The agent can be suspended in a liquid, e.g, in dissolved form or colloidal form. The liquid can be a solvent, partial solvent or non-solvent. In many cases water or an organic liquid can be used.

Administration of the agent can be alone or in combination with other therapeutic agents. In certain embodiments, the agent can be combined with a suitable carrier, incorporated into a liposome, or incorporated into a polymer release system.

In certain embodiments of the invention, the administration can be designed so as to result in sequential exposures to the agent over some time period, e.g., hours, days, weeks, months or years. This can be accomplished by repeated administrations of the agent by one of the methods described above, or alternatively, by a controlled release delivery system in which the agent is delivered to the mammal over a prolonged period without repeated administrations. By a controlled release delivery system is meant that total release of the agent does not occur immediately upon administration, but rather is delayed for some time period. Release can occur in bursts or it can occur gradually and continuously. Administration of such a system can be, e.g., by long acting oral dosage forms, bolus injections, transdermal patches and sub-cutaneous implants.

Examples of systems in which release occurs in bursts include, e.g, systems in which the agent is entrapped in liposomes which are encapsulated in a polymer matrix, the liposomes being sensitive to a specific stimuli, e.g., temperature, pH, light or a degrading enzyme, and systems in which the agent is encapsulated by an ionically-coated microcapsule with a microcapsule core-degrading enzyme. Examples of systems in which release of the agent is gradual and continuous include, e.g., erosional systems in which the agent is contained in a form within a matrix, and diffusional systems in which the agent permeates at a controlled rate, e.g., through a polymer. Such sustained release systems can be, e.g., in the form of pellets or capsules.

The invention also includes a method for identifying an agent useful for treating a mammal having a disease, e.g., an HIV infection, an autoimmune disease, an infectious disease or a malignancy. A mammal having lymphocytes and infected with a disease is provided. Lymphocytes include e.g., T cells and B cells. In certain embodiments, it is preferred that the lymphocytes are CD4-positive cells or CD8-positive cells. An agent is provided and administered to the mammal. It is determined if the agent alters the distribution or trafficking pattern of the lymphocytes in the mammal. An alteration in the distribution or trafficking pattern which results in a pattern which is more similar to that of a mammal which does not have the disease is correlated with the agent being useful for treating the mammal infected with the disease.

The invention also includes the agent obtainable by this method.

The invention further includes a method of utilizing an agent obtainable by this method to alleviate the symptoms of a disease in a mammal. A mammal having a disease is provided. An agent obtainable by the above described method is provided, and a therapeutically effective amount of the agent is administered to the mammal so as to alleviate the symptoms of the disease in the mammal. By therapeutically effective amount is meant that amount which is capable of at least partially preventing or reversing the symptoms of the disease. A therapeutically effective amount can be determined on an individual basis and will be based, at least in part, on consideration of the species of mammal, the mammal's size, the agent used, the type of delivery system used, the time of administration relative to the progression of the HIV infection, and whether a single, multiple, or controlled release dose regimen is employed. A therapeutically effective amount can be determined by one or ordinary skill in the art employing such factors and using no more than routine experimentation.

The invention also includes a method for treating a mammal having a disease. A mammal having lymphocytes, e.g., T cells or B cells is provided. In certain embodiments, it is preferred that the lymphocytes are CD4-positive cells or CD8-positive cells. The mammal provided also has a disease, e.g., an HIV infection, an autoimmune disease, an infectious disease, or a malignancy. The mammal is tested for an alteration in the distribution or trafficking of the lymphocytes as compared to a standard. Preferably, the lymphocyte distribution and trafficking is determined by the methods described above. If the distribution or trafficking of the lymphocytes is altered in the mammal having the disease, then a therapeutically effective amount of an agent which results in at least partially normalizing the altered distribution or trafficking of the lymphocytes is administered. The standard can be, e.g., a distribution or trafficking pattern obtained from an earlier determination of the disease-infected mammal, or a pattern obtained from another mammal not having the disease. The following non-limiting examples further illustrate the present invention.

EXAMPLES

Example 1: Preparation of $^{111}$In Labeled Antibody

This example illustrates the radiolabeling of a rat IgG$_{2b}$ monoclonal antibody directed against murine CD4 antigen with $^{111}$In.

Crude ascites having GK1.5, a rat IgG$_{2b}$ monoclonal antibody (Rafik, R. M. et al., Clin. Immunol. & Immunopathol. 52:486–506 (1989)) directed against the murine CD4 antigen (Dialynas, D. P. et al., J. Immunol. 131:2445–2451 (1983)), was used. Rat IgG was isolated from the ascites by a two step method of ammonium sulfate precipitation, followed by protein G purification, as described in Harlow, E. and Lane, E., Antibodies a Laboratory Manual, Cold Spring Harbor Laboratory, chapter 8:283–318 (1988). HPLC analysis of the resulting protein solution using a size exclusion column revealed a single protein peak which eluted with a retention time corresponding to monomeric IgG.

This antibody was conjugated with diethylenetriamine pentaacetic acid (DTPA) by the carboxy-carbonic anhydride method (Krejcarek, G. E. and Tucker, K. L., Biochem. Biophys. Res. Comm. 77:581–585 (1977); Khaw, B. A. et al., Hybridoma 3:11–23 (1984)). The DPTA-antibody conjugate was diluted to 2 mg of protein per millimeter (in 0.9% sodium chloride for injection, U.S. Pharmacopeia) and sterilized by membrane filtration. Aliquots of 0.1 ml were transferred aseptically to 2 ml sterile and pyrogen-free vials and stored at 4° C. for subsequent labeling with $^{111}$In.

The DTPA-antibody conjugate was radiolabeled with sterile, pyrogen-free $^{111}$In chloride as follows: GK1.5-DTPA (50 $\mu$L, 100 $\mu$g) was mixed with 50 $\mu$L of 1N sodium citrate, pH 5.3 and 5 $\mu$L (~3 mCi) of $^{111}$In chloride (NEZ 304, DuPont NEN Research Products, Boston, Mass.) was added. The solution was incubated at room temperature for 4 hours and the radiolabeled protein was separated on a 1×30 cm size-exclusion column (Sephadex G-25-80) eluted with 0.9% sodium chloride.

Example 2: CD4 Binding Assay

This example illustrates that the DTPA-antibody conjugate from Example 1 bound to CD4 with high specificity, as measured by fluorescence activated cell sorting. The DTPA-conjugated GK1.5 from Example 1 was tested in vitro to confirm that it had not lost its ability to bind with high specificity to CD4 expressed on murine splenocytes. Splenocytes harvested from C57/BL mice (Jackson Labs, Bar Harbor, Me.) were incubated with DTPA-GK1.5 (5 $\mu$g/ml) or a control isotype matched antibody directed against murine CD4 (clone YTS 191.1). The splenocyte-antibody complexes were then incubated with anti-Rat IgG$_{2b}$ antibody conjugated with FITC (Pharmingen, San Diego, Calif.) and analyzed by fluorescence activated cell sorting (FACSCAN, Becton Dickinson, Franklin Lakes, N.J.).

Fluorescence activated cell scan analysis indicated that an equivalent number of CD4 cells, as a fraction of total splenocytes, could be detected with both DTPA-GK1.5 and the control antibody. Furthermore, when bound to CD4$^+$ splenocytes, DTPA-GK1.5 was detected by anti-Rat IgG$_{2b}$-FITC with equal or greater fluorescence intensity compared with the control antibody.

Example 3: Imaging, Biodistribution and Statistical Methods

This example illustrates the imaging, biodistribution and statistical methods used in subsequent Examples. Groups of normal C57/BL and CD4 knockout mice weighing ~25 grams (Jackson Laboratories, Bar Harbor, Me.) were used in the following Examples. All radiopharmaceuticals were injected intravenously via the tail vein and biodistribution/gamma camera imaging was performed as follows: Six normal C57/BL mice were injected with 10 $\mu$Ci of $^{111}$In labeled GK1.5 containing 0.4, 9.7, or 99.7 $\mu$g of antibody protein. At 24 hours post-injection the animals were sacrificed by anesthesia overdose, and the organs removed for biodistribution studies. Samples of blood, liver, spleen, thymus, mesentery, kidney, bone, and lymph nodes were weighed and radioactivity was measured with a well type gamma counter (LBK model #1282 Wallae Oy, Finland). To correct for radioactive decay, aliquots of the injected doses were counted simultaneously. The results were expressed as percentage injected dose per gram (% ID/g).

Three additional normal C57/BL mice were injected with 100 μCi of $^{111}$In labeled GK1.5 containing 13, 22, or 112 μg of antibody protein. At 24 hours post-injection the animals were anesthetized with ether and whole body scintigrams were acquired using a large field of view gamma camera equipped with a pin-hole collimator containing a 3 mm insert and interfaced to a dedicated computer system (Technicare 410/Technicare 560, Solon, Ohio). Images were recorded for a preset time of 5 minutes per view with windows centered on the 174 and 247 KeV photopeaks of $^{111}$In.

The results of all experiments were evaluated by analysis of variance using a linear model in which tissue and antibody dose or CD4 status (normal C57/BL or CD4 knockout) were the classification variables (%ID/g=tissue+antibody dose+tissue* antibody dose or %ID/g=tissue+CD4 status+ tissue* CD4 status. Post hoc comparisons of individual means were performed by Duncan's new multiple range test (Duncan, D. B., Biometrics 11:1–42 (1955)). All results are expressed as mean ± S.D.

Example 4: Method for Measuring the Effect of the Specific Activity of $^{111}$In Labeled Anti-CD4 Monoclonal Antibody on Biodistribution and Imaging This example illustrates the protocol used to measure the effect of the specific activity of $^{111}$In labeled anti-CD4 monoclonal antibody on the biodistribution and gamma camera imaging in mice injected with this antibody.

Six normal C57/BL mice were injected with 10 μCi of $^{111}$In labeled anti-CD4 monoclonal antibody (GK1.5) from Example 1, containing 0.4, 9.7, or 99.7 μg of antibody protein. At 24 hours post-injection, the animals were sacrificed by anesthesia overdose, and the organs removed for biodistribution studies. Samples of blood, liver, spleen, thymus, mesentery, kidney, bone, and lymph nodes were weighed and radioactivity was measured with a well type gamma counter (LBK model #1282, Wallae Oy, Finland). To correct for radioactive decay, aliquots of the injected doses were counted simultaneously. The results were expressed as percentage injected dose per gram (% ID/g).

Three additional normal C57/BL mice were injected with 100 μCi of $^{111}$In labeled anti-CD4 monoclonal antibody (GK1.5) from Example 1, containing 13, 22, or 112 μg of antibody protein. At 24 hours post-injection, the animals were anesthetized with ether and whole body scintigrams were acquired using a large field of view gamma camera equipped with a pin-hole collimator containing a 3 mm insert and interfaced to a dedicated computer system (Technicare 410/Technicare 560, Solon, Ohio). Images were recorded for a preset time of 5 min per view with windows centered on the 174 and 247 KeV photopeaks of $^{111}$In.

Example 5: Method for Measuring the Effect of CD4 Gene Expression on Biodistribution and Imaging This example illustrates the protocol used to measure the effect of CD4 gene expression on the biodistribution and gamma camera imaging in mice injected with $^{111}$In labeled anti-CD4 monoclonal antibody.

Normal C57/BL and CD-4 knockout mice (n=6/group) were injected with 100 μCi of $^{111}$In labeled anti-CD4 monoclonal antibody (GK1.5) from Example 1, containing 5.4 μg of protein, and gamma camera imaging/ biodistribution measurements were performed as described in Example 3. The animals were imaged at both 24 and 45 hours after injection. In one additional normal mouse, imaging was performed at 60 hours after injection.

Example 6: The Effect of Specific Activity of $^{111}$In Labeled Anti-CD4 Monoclonal Antibody and CD4 Gene Expression on Biodistribution and Imaging This example illustrates (i) that the amount of accumulation of a labeled monoclonal antibody in different tissues of the body is dependent on the dose of labeled monoclonal antibody administered, and the tissue being measured; (ii) that the amount of accumulation of a labeled monoclonal antibody in different tissues is dramatically affected by the presence or absence of CD4; (iii) that the distribution of labeled monoclonal antibody in different tissues can be measured by gamma camera imaging, and that these images reflect the specific activity of the labeled monoclonal antibody administered, and whether or not CD4 is present or absent in the body.

Biodistribution measurements performed at 24 hours after injection of $^{111}$In-labeled anti-CD4 monoclonal antibody (GK1.5) into normal mice, as described in Example 4, demonstrated particularly high concentrations of antibody associated radioactivity in the spleen and lymph nodes, approximately 176% and 48% injected dose per gram. When increasing quantities of unlabeled antibody were added to a fixed amount radiolabeled antibody (thus decreasing specific activity) there was a dose dependent decrease in the amount of radiolabeled antibody that localized in these tissues.

Analysis of variance demonstrated significant main effects of tissue (p<0.001), antibody dose (p<0.001) and tissue by antibody dose interaction (p<0.001). The highest concentrations of radiolabeled antibody were detected in spleen and lymph nodes (p<0.001). In spleen, there was a clear dose dependent decrease in accumulation when specific activity was reduced. In contrast, accumulation of antibody in lymph nodes was higher with the intermediate vs high specific activity preparations (p<0.01) but lowest with the low specific activity preparations (p<0.01).

When similar studies were performed at 45 hours after injection of the radiolabeled monoclonal antibody in normal and CD4 knockout mice, as described in Example 5, a striking difference in biodistribution was observed. Analysis of variance demonstrated significant main effects of tissue (p<0.001), antibody dose (p<0.001) and tissue by antibody dose interaction (p<0.001). In the normal mice, the concentrations of radiolabel in the spleen and lymph nodes was 10–20 fold greater than in the corresponding tissues of the CD4 knockout mice (p<0.0001); and 10–20 fold greater than the concentrations achieved in nonlymphoid tissues of both normal and CD4 knockout mice (p<0.0001)

These two biodistribution studies suggest that the localization of the radiolabeled anti-CD4 monoclonal antibody in lymphoid tissue of the mouse is mediated by specific, rather than nonspecific mechanisms. Furthermore, the differences in tissue accumulation of radiolabeled antibody were clearly sufficient to permit noninvasive imaging of the distribution of this antibody.

Gamma camera images of normal mice were acquired at 24 hours after injection of the radiolabeled antibody at three different levels of specific activity, 0.0507 μCi/μg, 0.507 μCi/μg, and 5.07 μCi/μg, as described in Example 4. The image acquired with the highest specific activity antibody preparation shows clear focal accumulation of radioactivity in the spleen and lymph nodes. This focal localization of radioactivity was significantly reduced in the intermediate specific activity image and totally abolished in the low specific activity image. Thus, competitive inhibition of the localization of labeled antibody by increasing concentrations of unlabeled antibody was clearly evident.

Serial gamma camera images were acquired at three time points, 3.5, 24 and 44 hours, after injection of the radiolabeled antibody in normal and CD4 knockout mice. These images demonstrated that there was a high degree of localization of radiolabeled antibody in the lymph nodes and spleen of the normal mice which was not evident in the CD4 knockout mice.

Example 7: The Effect, as Measured by Imaging, on the Biodistribution and Trafficking Patterns in HIV-Infected Individuals Using $^{111}$In Labeled Anti-CD4 Monoclonal Antibody This example illustrates that HIV-infected individuals have altered CD4 cell distribution and trafficking patterns.

A murine anti-human CD4 monoclonal antibody, GK1.5, is used for these imaging studies (Ortho Biotech, Raritan, N.J.). This monoclonal antibody is conjugated with DTPA by the carboxy-carbonic anhydride method (Krejcarek, G. E. and Tucker, K. L., Biochem. Biophys. Res. Comm., 77:581–585 (1977); Khaw, B. A. et al., Hybridoma, 3:11–23 (1984)), and is acquitted into 0.1 ml volumes. One lot of DTPA coupled antibody that is shown to be sterile, apyrogenic, and to fulfill general safety requirements for human use is used. Aliquots are studied for their binding characteristics in vitro with different human leukocyte fractions, to demonstrate specificity of the antibody after labeling. On the day of the imaging procedure, the DTPA conjugated monoclonal antibody is labeled with sterile, pyrogen free indium-111 by citrate transchelation, with radiochemical purity determined following this step by thin-layer chromatography (Rubin, R. H. et al., N. Engl. J. Med. 321:935–940 (1989)).

The $^{111}$In anti-CD4 monoclonal antibody is used in two series of experiments: (i) biodistribution: infusion into a human subject of 0.025 mg antibody/kg body weight labeled with approximately 56 MBq (1.5 mCi) of indium-111 intravenously; and (ii) trafficking: infusion into a human subject of approximately $10^7$ leukocytes labeled in vitro with the same $^{111}$In-labeled antibody. Control reagents in these studies are standard $^{111}$In-labeled nonspecific IgG and indium-oxine labeled leukocytes. (McAfee, J. G. and Thakur, M. L., J. Nucl. Med. 17:480–487 (1976)). Following infusion, total body image scans of the subjects are carried out 5 min, 5 hrs, 12 hrs, 24 hrs, 48 hrs, and 96 hrs post-infusion, with blood drawn for in vitro immunologic studies drawn prior to infusion, and then at the time of each of the gamma camera scans. In addition, the following additional laboratory studies are carried out: complete blood count, differential and counts of CD3, CD4, and CD8 lymphocytes.

All patients are evaluated using the viral RNA test (Saksela, K. et al., Proc. Natl. Acad. Sci. USA 91:1104–1108 (1994)). In that way, the lymphocyte localizations are correlated with the predicted prognosis of the patient.

Subjects in each of the following four categories are studied: normal volunteers; HIV infected individuals with a CD4 count of >500/mm$^3$; HIV infected individuals with a CD4 count of 200–499/mm$^3$; HIV infected individuals with a CD4 count of 100–200/mm$^3$; and HIV infected individuals with a CD4 count of <99/mm$^3$. All individuals are free of active non-HIV infection for >1 month prior to study entry.

Scans are interpreted blindly, without knowledge of the individual's clinical, immunologic, or virologic status. Particular information sought from the scans includes the delineation of human lymphoid tissue known to harbor large numbers of CD4-positive lymphocytes (e.g. nodes, spleen and gut-associated lymphoid tissue). The results of the scan interpretations are correlated to the viral and immunologic data.

The scans for HIV-infected individuals with lowered CD4 cell counts show altered CD4 cell distribution and trafficking as compared to normal individuals. The results also provide a comprehensive view of CD4 cell distribution and trafficking in HIV-infected people at different stages of their disease.

Those skilled in the art will be able to ascertain, using no more than routine experimentation, many equivalents of the specific embodiments of the invention described herein. These and all other equivalents are intended to be encompassed by the following claims.

What is claimed is:

1. A method for determining lymphocyte distribution in a mammal having an HIV infection, said method comprising:
   providing a mammal having lymphocytes, said mammal having an HIV infection;
   providing labeled ligand capable of interacting specifically with said lymphocytes;
   administering said labeled ligand to said mammal under conditions which allow said labeled ligand to interact with said lymphocytes so as to result in labeled lymphocytes; and
   determining the distribution of said labeled lymphocytes in said mammal by imaging.

2. The method of claim 1 wherein said lymphocytes are selected from the group consisting of T cells and B cells.

3. The method of claim 1 wherein said lymphocytes are selected from the group consisting of CD4-positive cells and CD8-positive cells.

4. The method of claim 1 wherein said ligand is capable of interacting specifically with said lymphocytes as a result of said ligand interacting with a lymphocyte surface antigen.

5. The method of claim 1 wherein said ligand is selected from the group consisting of an antibody, an antibody fragment and a recombinant antibody.

6. The method of claim 5 wherein said antibody is a monoclonal antibody.

7. The method of claim 6 wherein said monoclonal antibody is anti-CD4 monoclonal antibody.

8. The method of claim 1 wherein said ligand is selected from the group consisting of a peptide, a peptide mimetic, a carbohydrate, and a glycoprotein.

9. The method of claim 1 wherein the label in said labeled ligand is selected from the group consisting of a gamma emitter, a positron emitter, a magnetic material, a density based contrast material, and mixtures thereof.

10. The method of claim 1 wherein the label in said labeled ligand is a gamma emitter selected from the group consisting of indium-111, technetium-99m, technetium-99, iodine-123, and mixtures thereof.

11. The method of claim 1 wherein the label in said labeled ligand is indium-111.

12. The method of claim 1 wherein the label in said labeled ligand is a positron emitter selected from the group consisting of fluorine-18, carbon-11, iodine-124, and mixtures thereof.

13. The method of claim 1 wherein the label in said labeled ligand is a magnetic material selected from the group consisting of gadolinium, a superparamagnetic substance, a hydrated iron oxide particle, and mixtures thereof.

14. The method of claim 1 wherein the label in said labeled ligand is a density based contrast material.

15. The method of claim 1 wherein said imaging is selected from the group consisting of radioimaging, magnetic resonance imaging and computed tomographic imaging.

16. The method of claim 1 wherein said imaging is selected from the group consisting of a single scan and serial scans.

17. The method of claim 1 wherein said imaging comprises a total body scan of said mammal.

18. A method for determining lymphocyte trafficking in a mammal having an HIV infection, comprising:
   providing a first mammal having an HIV infection;
   providing a cell population having lymphocytes;
   providing labeled ligand capable of interacting specifically with said lymphocytes;
   contacting said lymphocytes in vitro with said labeled ligand under conditions which allow said ligand to interact with said lymphocytes so as to result in labeled lymphocytes;
   administering said labeled lymphocytes into said first mammal; and
   determining the trafficking of said labeled lymphocytes in said first mammal by imaging.

19. The method of claim 18 wherein said cell population is obtained from said first mammal.

20. The method of claim 18 wherein said cell population is obtained from a second mammal.

21. The method of claim 18 wherein said lymphocytes are selected from the group consisting of T cells and B cells.

22. The method of claim 18 wherein said lymphocytes are selected from the group consisting of CD4-positive cells and CD8-positive cells.

23. The method of claim 18 wherein said ligand is capable of interacting specifically with said lymphocytes as a result of said ligand interacting with a lymphocyte surface antigen.

24. The method of claim 18 wherein said ligand is selected from the group consisting of an antibody, an antibody fragment and a recombinant antibody.

25. The method of claim 24 wherein said antibody is a monoclonal antibody.

26. The method of claim 25 wherein said monoclonal antibody is anti-CD4 monoclonal antibody.

27. The method of claim 18 wherein said ligand is selected from the group consisting of a peptide, a peptide mimetic, a carbohydrate, and a glycoprotein.

28. The method of claim 18 wherein the label in said labeled ligand is selected from the group consisting of a gamma emitter, a positron emitter, a magnetic material, a density based contrast material, and mixtures thereof.

29. The method of claim 18 wherein the label in said labeled ligand is a gamma emitter selected from the group consisting of indium-111, technetium-99m, technetium-99, iodine-123, and mixtures thereof.

30. The method of claim 18 wherein the label in said labeled ligand is indium-11.

31. The method of claim 18 wherein the label in said labeled ligand is a positron emitter selected from the group consisting of fluorine-18, carbon-11, iodine-124, and mixtures thereof.

32. The method of claim 18 it wherein the label in said labeled ligand is a magnetic material selected from the group consisting of gadolinium, a superparamagnetic substance, a hydrated iron oxide particle, and mixtures thereof.

33. The method of claim 18 wherein the label in said labeled ligand is a density based contrast material.

34. The method of claim 18 wherein said imaging is selected from the group consisting of radioimaging, magnetic resonance imaging and computed tomographic imaging.

35. The method of claim 18 wherein said imaging is selected from the group consisting of a single scan and serial scans.

36. The method of claim 18 wherein said imaging comprises a total body scan of said mammal.

37. The method of claim 18 wherein said lymphocytes that are contacted in vitro with said labeled ligand are in a mixed cell population.

38. A method for diagnosing the degree of progression of an HIV infection in a mammal, comprising:
   providing a first mammal having lymphocytes, said first mammal having an HIV infection;
   determining the distribution or trafficking pattern of said lymphocytes in said first mammal by imaging, wherein the determining step comprises providing labeled ligand capable of interacting specifically with said lymphocytes and administering said labeled ligand to said first mammal under conditions which allow said labeled ligand to interact with said lymphocytes so as to result in labeled lymphocytes; and
   comparing said distribution or trafficking pattern to a standard so as to diagnose the degree of progression of said HIV infection.

39. The method of claim 38 wherein said lymphocytes are selected from the group consisting of T cells and B cells.

40. The method of claim 38 wherein said lymphocytes are selected from the group consisting of CD4-positive cells and CD8-positive cells.

41. The method of claim 38 wherein said standard is a distribution or trafficking pattern of a second mammal not having said HIV infection.

42. The method of claim 38 wherein said standard is a distribution or trafficking pattern obtained from an earlier determination from said first mammal.

43. The method of claim 38 wherein the determining step comprises:
   providing a cell population having lymphocytes;
   providing labeled ligand capable of interacting specifically with said lymphocytes;
   contacting said lymphocytes in vitro with said labeled ligand under conditions which allow said labeled ligand to interact with said lymphocytes so as to result in labeled lymphocytes;
   administering said labeled lymphocytes to said first mammal; and
   determining the trafficking of said labeled lymphocytes in said first mammal by imaging.

44. A method for monitoring the response to a therapy in a mammal having an HIV infection, comprising:
   providing a first mammal having lymphocytes, said first mammal having an HIV infection;
   treating said first mammal with a therapy for said HIV infection; and
   monitoring the response of said first mammal to said treating step by determining whether said therapy alters the distribution or trafficking pattern of said lymphocytes in said first mammal by imaging.

45. The method of claim 44 wherein said lymphocytes are selected from the group consisting of T cells and B cells.

46. The method of claim 44 wherein said lymphocytes are selected from the group consisting of CD4-positive cells and CD8-positive cells.

47. The method of claim 44 wherein said determining step comprises:

provinding labeled ligand capable of interacting specifically with said lymphocytes;

administering said labeled ligand to said first mammal under conditions which allow said labeled ligand to interact with said lymphocytes so as to result in labeled lymphocytes; and determining the distribution of said labeled lymphocytes in said first mammal by imaging.

48. The method of claim 44 wherein said determining step comprises:

providing a cell population having lymphocytes;

providing labeled ligand capable of interacting specifically with said lymphocytes from said cell population;

contacting said lymphocytes from said cell population in vitro with said labeled ligand under conditions which allow said labeled ligand to interact with said lymphocytes from said cell population so as to result in labeled lymphocytes;

administering said labeled lymphocytes to said first mammal; and determining the trafficking of said labeled lymphocytes in said first mammal by imaging.

49. The method of claim 48 wherein said lymphocytes in said cell population are obtained from said first mammal.

50. The method of claim 48 wherein said lymphocytes in said cell population are obtained from a second mammal.

51. A method for evaluating the ability of an agent to alter the distribution or trafficking of lymphocytes in a mammal having an HIV infection, comprising:

providing a first HIV infected mammal having lymphocytes;

providing an agent;

administering said agent to said first mammal; and determining whether said agent alters the distribution or trafficking of said lymphocytes in said first mammal.

52. The method of claim 51 wherein said lymphocytes are selected from the group consisting of T cells and B cells.

53. The method of claim 51 wherein said lymphocytes are selected from the group consisting of CD4-positive cells and CD8-positive cells.

54. The method of claim 51 wherein said determining step comprises:

providing labeled ligand capable of interacting specifically with said lymphocytes;

administering said labeled ligand to said first mammal under conditions which allow said labeled ligand to interact with said lymphocytes so as to result in labeled lymphocytes; and determining the distribution of said labeled lymphocytes in said first mammal by imaging.

55. The method of claim 51 wherein said determining step comprises:

providing a cell population having lymphocytes;

providing labeled ligand capable of interacting specifically with said lymphocytes from said cell population;

contacting said lymphocytes from said cell population in vitro with said labeled ligand under conditions which allow said labeled ligand to interact with said lymphocytes from said cell population so as to result in labeled lymphocytes;

administering said labeled lymphocytes to said first mammal; and determining the trafficking of said labeled lymphocytes in said first mammal by imaging.

56. The method of claim 55 wherein said lymphocytes in said cell population are obtained from said first mammal.

57. The method of claim 55 wherein said lymphocytes in said cell population are obtained from a second mammal.

58. A method for identifying an agent useful for treating a mammal having an HIV infection, comprising:

providing an HIV infected mammal having lymphocytes;

providing an agent;

administering said agent to said mammal; and determining whether said agent alters the distribution or trafficking of said lymphocytes in said first mammal, an alteration in said distribution or trafficking pattern which results in a distribution or trafficking pattern more similar to that of a mammal which does not have said disease being correlated with said agent being useful for treating said mammal having said disease.

59. The method of claim 58 wherein said lymphocytes are selected from the group consisting of T cells and B cells.

60. The method of claim 58 wherein said lymphocytes are selected from the group consisting of CD4-positive cells and CD8-positive cells.

* * * * *

UNITED STATES PATENT AND TRADEMARK OFFICE
CERTIFICATE OF CORRECTION

PATENT NO. : 6,146,614
DATED : November 14, 2000
INVENTOR(S) : Robert H. Rubin, Alan J. Fischman and David Baltimore It is certified that error appears in the above-identified patent and that said Letters Patent is hereby corrected as shown below:

Column 12,
Line 37, "(p<0.001)" should be -- (p<0.01) --

Column 13,
Line 41, "biodistribution" should be -- biodistribution --
Line 44, "trafficking" should be -- trafficking --

Signed and Sealed this

Twenty-fifth Day of June, 2002

Attest:

JAMES E. ROGAN
Attesting Officer   Director of the United States Patent and Trademark Office